(12) United States Patent
Pommereau et al.

(10) Patent No.: US 8,773,660 B2
(45) Date of Patent: Jul. 8, 2014

(54) ARRANGEMENT FOR DETERMINING A LONGITUDINAL POSITION OF A STOPPER

(75) Inventors: Christian Pommereau, Frankfurt (DE); Anke Liewald, Frankfurt (DE); Nils Basso, Frankfurt (DE); Thomas Nagel, Tharandt (DE); René Richter, Tharandt (DE); Robert Witt, Dresden (DE)

(73) Assignee: Sanofi—Aventis Deutschland GmbH, Frankurt am Main (DE)

( * ) Notice: Subject to any disclaimer, the term of this patent is extended or adjusted under 35 U.S.C. 154(b) by 216 days.

(21) Appl. No.: 13/393,329

(22) PCT Filed: Sep. 15, 2010

(86) PCT No.: PCT/EP2010/063514
§ 371 (c)(1),
(2), (4) Date: Jul. 12, 2012

(87) PCT Pub. No.: WO2011/032960
PCT Pub. Date: Mar. 24, 2011

(65) Prior Publication Data
US 2012/0268741 A1    Oct. 25, 2012

(30) Foreign Application Priority Data
Sep. 18, 2009    (EP) .................................... 09170689

(51) Int. Cl.
*G01N 21/00*    (2006.01)
(52) U.S. Cl.
USPC ....................................................... 356/343
(58) Field of Classification Search
CPC ................................ G01N 21/00; G01B 11/14
USPC .................. 356/343, 614, 616, 620, 622, 623
See application file for complete search history.

(56) References Cited

U.S. PATENT DOCUMENTS 3,774,603 A * 11/1973 McPhee .................... 604/246
4,733,095 A *  3/1988 Kurahashi et al. ........... 250/577
(Continued)

FOREIGN PATENT DOCUMENTS

DE        10226643      1/2004
DE      102006047537    4/2008
(Continued)

OTHER PUBLICATIONS

International Search Report for International App. No. PCT/EP2010/063514, completed Jan. 31, 2011.

(Continued)

*Primary Examiner* — Roy M Punnoose
(74) *Attorney, Agent, or Firm* — McDonnell Boehnen Hulbert & Berghoff LLP

(57) ABSTRACT

The invention refers to an arrangement and a method for determining a longitudinal position of a stopper for sealing a compartment of a translucent medicament container for a liquid medicament (M). The arrangement comprises a circular light source and a photo sensitive sensor, wherein either the light source or the sensor is laterally arrangeable next to the medicament container extending over at least part of the length of the medicament container, and wherein the respective other of the light source and the sensor is arrangeable in a circular manner around a head of the medicament container. The light source is arranged to emit light into the medicament container. The light is scattered by the medicament or medicament container and detected by the sensor. The sensor is connected to a processor unit for detecting the position of the stopper).

19 Claims, 6 Drawing Sheets

(56) References Cited

U.S. PATENT DOCUMENTS

| | | | | |
|---|---|---|---|---|
| 4,956,560 | A * | 9/1990 | Smith et al. | 250/577 |
| 5,310,658 | A * | 5/1994 | Berndt | 435/34 |
| 5,463,228 | A * | 10/1995 | Krause | 250/577 |
| 5,523,560 | A * | 6/1996 | Manique et al. | 250/223 B |
| 5,782,814 | A * | 7/1998 | Brown et al. | 604/207 |
| 5,954,700 | A * | 9/1999 | Kovelman | 604/232 |
| 6,027,472 | A * | 2/2000 | Kriesel et al. | 604/89 |
| 6,068,615 | A | 5/2000 | Brown et al. | |
| 6,110,152 | A * | 8/2000 | Kovelman | 604/232 |
| 6,448,574 | B1 * | 9/2002 | Chow | 250/577 |
| 6,685,678 | B2 * | 2/2004 | Evans et al. | 604/207 |
| 7,470,259 | B2 * | 12/2008 | Hoyle, Jr. | 604/207 |
| 7,499,581 | B2 * | 3/2009 | Tribble et al. | 382/141 |
| 7,604,985 | B2 * | 10/2009 | Bachur et al. | 435/288.7 |
| 7,614,545 | B2 * | 11/2009 | Christoffersen et al. | 235/375 |
| 8,208,141 | B2 * | 6/2012 | Schmidt et al. | 356/402 |
| 2002/0087121 | A1 * | 7/2002 | Slishman | 604/189 |
| 2003/0125670 | A1 | 7/2003 | Langley et al. | |
| 2004/0021100 | A1 | 2/2004 | Gouzman et al. | |
| 2004/0082918 | A1 * | 4/2004 | Evans et al. | 604/207 |
| 2004/0162528 | A1 * | 8/2004 | Horvath et al. | 604/207 |
| 2006/0126060 | A1 * | 6/2006 | Colle et al. | 356/239.4 |
| 2006/0154327 | A1 * | 7/2006 | Bachur et al. | 435/34 |
| 2007/0075228 | A1 | 4/2007 | Engstrand | |
| 2009/0137949 | A1 | 5/2009 | Landau et al. | |
| 2010/0145274 | A1 * | 6/2010 | Royce | 604/132 |

FOREIGN PATENT DOCUMENTS

| | | |
|---|---|---|
| EP | 1260244 | 11/2002 |
| EP | 1911479 | 4/2008 |
| WO | 98/00187 | 1/1998 |
| WO | 98/03215 | 1/1998 |
| WO | 01/56635 | 8/2001 |
| WO | 02/083209 | 10/2002 |

OTHER PUBLICATIONS

International Preliminary Report on Patentability for International App. No. PCT/EP2010/063514, issued Mar. 20, 2012.

* cited by examiner

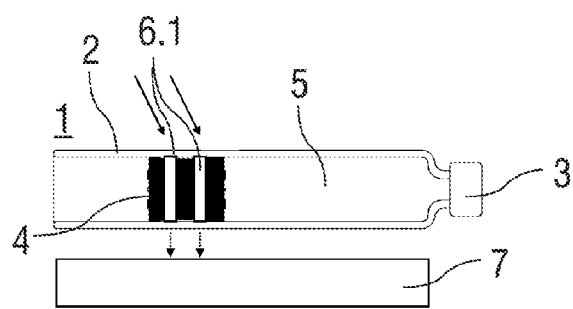
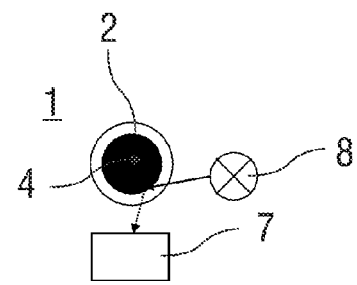
FIG 8a  FIG 8b
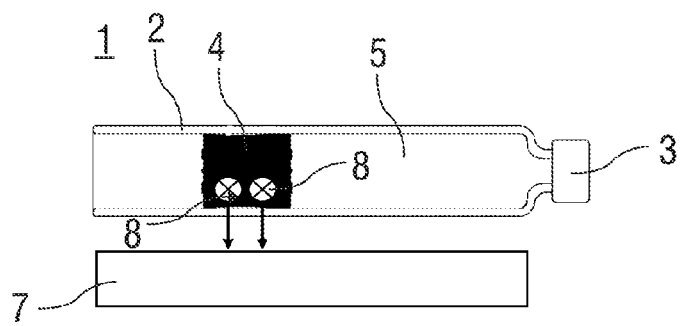
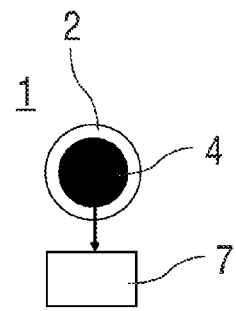
FIG 9a  FIG 9b

ARRANGEMENT FOR DETERMINING A LONGITUDINAL POSITION OF A STOPPER

CROSS REFERENCE TO RELATED APPLICATIONS

The present application is a U.S. National Phase Application pursuant to 35 U.S.C. §371 of International Application No. PCT/EP2010/063514 filed Sep. 15, 2010, which claims priority to European Patent Application No. 09170689.5 filed on Sep. 18, 2009. The entire disclosure contents of these applications are herewith incorporated by reference into the present application.

FIELD OF INVENTION

The invention refers to an arrangement for determining a longitudinal position of a stopper for sealing a compartment of a medicament container.

BACKGROUND

Medicament containers such as syringes or ampoules usually comprise a hollow cylinder made of a pharmaceutical glass which is inert and chemically resistant against the drug stored inside, e.g. insulin. The container is sealed by a stopper or bung at one end of the cylinder which can be moved along the longitudinal axis of the cylinder in order to displace the drug and force it out of an outlet end which may be sealed by a piercable membrane. The stopper and the piercable membrane are conventionally made of an elastomere ensuring mechanical tightness under defined pressure conditions and long term germ impermeability. Other important parameters affecting the dimensioning and choice of materials of the stopper and the piercable membrane are the maximum force expected at the stopper and the number of allowable piercings of the piercable membrane.

Before filling in the drug and sealing the container, the quality of the inner surface of the cylinder is improved by siliconization, so static and dynamic frictions of the stopper are reduced. Furthermore siliconization improves the dosing accuracy and reduces the risk of glass particles being unhinged from the inner surface during long term storage.

DE 102 26 643 A1 discloses a stopper for an injection arrangement, the stopper comprising a stopper body, a stopper body support attached to a drive member of the injection arrangement and a sealing member for sealing a product container of the injection arrangement against the stopper body, wherein a membrane body is arranged in a cap-like manner at a proximal end of the stopper body wherein the sealing member is part of the membrane body. A sensor is provided for measuring a pressure exerted by the product on the proximal end of the membrane body. The sensor may be a pressure sensor.

US 2003/0125670 A1 discloses a medicament cartridge comprising a cylinder and a displaceable plunger. The cartridge is provided with an electrical element having specified electrical properties located on an external face of the plunger. The electrical element can take the form of a conductive disk or two conductive rings joined by a resistive pad. The device may be equipped with electrical contacts for contacting the electrical element.

WO 01/56635 discloses a container for a substance, which container comprises a coupling element for coupling the container with an administration unit for the substance, and a recognition element associated with the substance. The recognition element may be a bar code printed on a package, a chip card enclosed in the package or a magnetic card.

EP 1911479 A1 discloses a drug delivery device with magnetic connection between piston and piston rod. The device has a retaining volume for a product, and a piston movable in the retaining volume and/or relative to the retaining volume for discharging the product from the retaining volume. A piston rod is brought in effective connection with the piston. A coupling unit is provided in the piston for producing an electromagnetic or magnetic effect. The piston rod is provided with a permanent magnet, which produces an electromagnetic or magnetic effect. The piston and the piston rod are connected with each other by the coupling unit and the permanent magnet.

WO 9800187 A1 discloses a preparation delivery device comprising a) a container for the preparation having or being prepared for the arrangement of an opening, b) a mechanism operable to deliver at least part of the preparation in the container through the opening, c) attachment means for connection of the container to the mechanism and d) a sensor system arranged to detect at least one predetermined property of the container or its content. The device comprises a radiation transmitter arranged to irradiate the container position or a part thereof, a radiation receiver arranged to receive at least an area part of the radiation from the transmitter after the radiation has been affected by the container position and the receiver being designed to give an output response representative for the total radiation received from said area part. A method for operating the device comprises the step of transmitting radiation towards the container position or a part thereof to allow the radiation to be affected by the container position, receiving at least a part of the affected radiation from at least an area part of the container position in a non-imaging way and comparing the characteristics of the received radiation with a predetermined characteristic representative for the predetermined property to establish whether or not the predetermined property of the container is present.

US 2009137949 A1 discloses a nozzle assembly for a needle-free injection device. The nozzle assembly includes a nozzle body including an injectate chamber and one or more outlet orifices and a plunger configured to move through the injectate chamber toward the one or more outlet orifices. In some embodiments, the plunger includes a first portion and a second portion removably joined by a frangible region. In some embodiments, the plunger includes extensions configured to couple the plunger to a drive assembly of a needle-free injection device.

WO 02083209 A1 discloses a pump system for an infusion system includes a linear drive which minimizes the space occupied by the pump system in a portable housing. A motor and a motor drive shaft are arranged in parallel with, and adjacent to a syringe and lead screw. A gear box connects the drive shaft and lead screw to transfer rotational movements between them. A piston driving member, such as a cone or drive nut converts the rotational movement of the lead screw into linear motion of a syringe piston. Sensors detect when the piston or cone is in a "home" position and in an "end" position, respectively. A clamping member selectively clamps the lead screw against linear motion in at least a dispensing direction. Optionally, a proximity sensor is used to ensure that the cone and the piston are abutting during dispensing.

WO 9803215 A1 discloses means for optical dose measurements in syringes. Measurements of insulin quantities in a syringe are performed optically in an integrated insulin dose recorder/blood glucose meter. The syringe is placed in a holder before and after the administration of the dose. Liquid quantities in the syringe are determined by comparing optical response patterns of the syringe with calibration data stored in the device. Dose histories are downloaded to a patient computer for transfer to a clinician's computer. Standard or customized syringes (e.g., with marked plungers) may be used. Other wave energy carriers such as sound waves may also be used.

EP 1260244 A2 discloses a method of monitoring performance of an osmotic drug delivery system comprises implanting an osmotic drug delivery device having a movable piston in an animal, and determining a position of the implanted movable piston within the osmotic drug delivery device from an exterior of the animal. The position of the movable piston may be determined either by fluoroscopy, by X-ray, or by a magnetic gauge. The osmotic delivery device preferably comprises an implantable reservoir having at least one opening for delivering a beneficial agent contained within an interior of the reservoir to an organ of the animal, and an osmotic engine causing the release of the beneficial agent contained within the reservoir to the animal.

U.S. Pat. No. 6,068,615 discloses arrangements for inductance-based dose measurement in syringes. Measurements of insulin quantities in a syringe are performed inductively in an integrated insulin dose recorder/blood glucose meter. The syringe is placed in a holder before the administration of the dose, and the liquid quantity in the syringe is recorded. Inductors may be situated within the syringe and/or outside the syringe in various geometries. Standard or customized syringes may be used. Liquid quantities in the syringe are determined by comparing inductive response patterns of the syringe with calibration data stored in the device. Insulin dose and blood glucose histories are downloaded to a patient computer for transfer to a clinician's computer.

SUMMARY

It is an object of the invention to provide an improved arrangement for determining a longitudinal position of a stopper for sealing a compartment of a medicament container.

The object is achieved by an arrangement with the features of the independent claim 1.

Advantageous embodiments are given in the dependent claims.

In the following the term proximal refers to a direction on a medicament container intended for attaching an outlet or an injection needle whereas the term distal refers to the opposite direction where a cylinder of the medicament container is open but sealed by a stopper.

According to the invention an arrangement for determining a longitudinal position of a stopper for sealing a compartment of a translucent medicament container for a liquid medicament comprises at least one light source and at least one photo sensitive sensor.

In the context of this specification the term translucent refers to a property of a material allowing at least partial transmission of light regardless of whether or not the light is scattered by the material or not. The term transparent by contrast refers to a condition where the light emitted from a light source on one side of the material is transmitted in a manner to create an image of the light source on the other side of the material, in other words to see through the material. In this sense, a transparent material is translucent, whereas a translucent material does not have to be necessarily transparent.

Either the at least one light source or the at least one sensor is laterally arrangeable next to the medicament container and extending over at least part of the length of the medicament container, preferably over at least almost the entire length.

The respective other of the at least one light source and the at least one sensor sensor is arrangeable in a circular manner around a head of the medicament container, i.e. near a proximal end. The light source is arranged to emit light into the medicament container. The medicament container and/or the medicament is arranged to scatter the light so as to allow the sensor to detect it. The at least one sensor is connectable to a processor unit for processing sensor data.

In one embodiment the light source may be a circular light source arrangeable around the head of the medicament container, wherein an array of photo sensitive sensors is laterally arrangeable next to the medicament container. The processor unit is arranged to determine the stopper position by detecting a light/dark boundary caused by the laterally scattered light and the opaque stopper.

In an alternative embodiment an array of light sources is laterally arrangeable next to the medicament container. Each light source emits light with a characteristic distinct from the characteristics of the other light sources. The at least one sensor is arrangeable around the head of the medicament container and able to detect the light of each light source. The processor unit has information on the allocation of each light source and its characteristic and its position in the array. The processor unit is arranged to:
   detect the characteristics of the light sources,
   determine which light source is currently emitting light into the medicament container,
   conclude, that the light sources whose characteristics are absent in the sensor data are currently obscured by the stopper,
   determine the stopper position by comparing these conclusions to the information on the allocation of the light sources, their characteristic and their position in the array.

The sensor may be arranged as a ring of sensors around the head of the medicament container.

The characteristic of each light source may be at least one wavelength or a range of wavelengths of the light. The characteristic of each light source may also be an individual a modulation of the light, such as a frequency or pattern of pulsed light, in order to make the light sources distinguishable.

In order to scatter the light from the at least one light source so as to allow the at least one sensor to detect the light, the medicament may be a cloudy liquid. Another approach for scattering the light could be a non-transparent medicament container, i.e. a medicament container, which is translucent but not transparent in order to scatter the light on its outer surface.

The processor unit may be arranged to determine a remaining quantity of the medicament in the medicament container from the longitudinal position of the stopper.

The arrangement may be part of an injection device.

In an example embodiment a stopper for sealing a compartment of a medicament container has at least one marker detectable through a lateral area of the medicament container. The stopper may be arranged in the medicament container moveably in a longitudinal direction. By detecting a longitudinal position of the marker a longitudinal position of the stopper can be determined with high accuracy provided the location of the marker with respect to the stopper dimensions is defined. Hence a remaining quantity of the medicament in the medicament container can be calculated for a given geometry of the medicament container and a given longitudinal position of the marker. This allows for an automatic dosing of the medicament, e.g. in an electromechanical insulin pen.

The marker may be a visual marker arranged in and/or on a lateral area of the stopper, the marker being distinguishable from the stopper material by its colour, e.g. by means of an optical sensor arranged outside the medicament container.

The visual marker may have the shape of a line or stripe or pattern. There may be more than one line or stripe arranged on the stopper, preferably in a circumferential direction of the stopper's lateral area. Thus the stopper may be rotated with respect to the sensor without affecting the accuracy of the determination of the longitudinal position.

The visual marker may be applied, e.g. printed onto or embedded into the lateral area of the stopper.

In another example embodiment the marker is a permanent magnet embedded in the stopper. A magnetic marker may be detected by a magnetic sensor, such as a Hall sensor. As opposed to the visual marker a magnetic marker does not require illumination in order to be detectable. Thus the longitudinal position may also be determined in poor lighting conditions or with medicaments which must not be exposed to light.

In yet another example embodiment the marker may be an electrically conductible marker embedded in the stopper, e.g. an iron core. Such a marker may be detected by inducing an electrical current and measuring the consequently altered magnetic field. This embodiment may also be used without illumination.

The stopper may be applied in an insulin pen injector, both for faster or slower reacting drugs. In this case the medicament container with the stopper is arranged inside the insulin pen. The sensor is arranged outside the medicament container but inside the insulin pen and connected to a processing unit for calculating the remaining quantity which can be displayed by an adequate means, e.g. an LED or LC display. The stopper may as well be applied in other injection devices and for different medicaments, e.g. anticoagulants.

The stopper according to either embodiment can comprise the same materials as conventional stoppers, such as elastomeres. The primary packaging, i.e. the glass cylinder of the medicament container may remain unchanged. Design modifications of the ampoule or the injection device are not required.

The medicament container may be a disposable device or a reusable device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 8 is a medicament container with a laterally arranged light source and a laterally arranged sensor, FIG. 9 is a medicament container and a stopper with an integrated light source.

DETAILED DESCRIPTION

Figure 1:
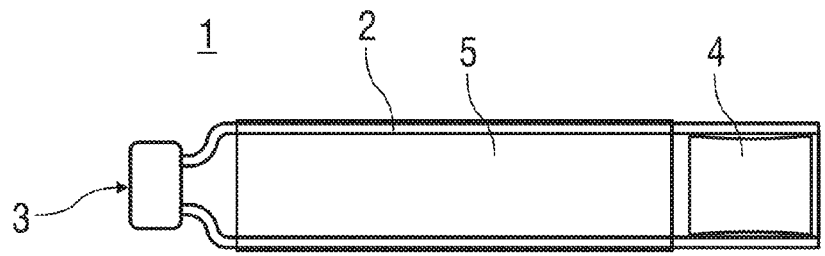
FIG. 1 is a conventional art medicament container with a glass cylinder sealed by a piercable membrane and a stopper.

FIG. 1 is a conventional art medicament container 1 with a hollow cylinder 2 sealed by a piercable membrane 3 and a stopper 4. The piercable membrane 3 and the stopper 4 define a compartment 5 between for holding a substance, e.g. a medicament M. FIG. 11 shows the location of medicament M that is present in each of the cylinders illustrated in FIGS. 1 and 5-14 having a longitudinal axis L, even though not schematically shown in FIGS. 1, 5-10 and 12-14. The cylinder 2 may consist of glass. The stopper 4 can be moved along the longitudinal axis L of the cylinder 2 in order to displace the medicament and force it out of an outlet positioned at head 50 provided the piercable membrane 3 is pierced. The stopper 4 and the piercable membrane 3 may be made of an elastomere. The medicament container may have a label indicating its content, e.g. insulin.

Figure 2:
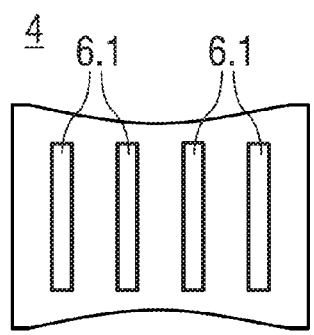
FIG. 2 is a stopper with a visual marker applied on a lateral area.

FIG. 2 is a stopper 4 with a number of visual markers 6.1 applied on a lateral area of the stopper 4. The visual marker 6.1 is detectable through a lateral area of the medicament container 1 which has to be transparent or translucent for this purpose. By detecting a longitudinal position of the visual marker 6.1 a longitudinal position of the stopper 4 can be determined with high accuracy provided the location of the visual marker 6.1 with respect to the stopper 4 dimensions is defined. Hence a remaining quantity of the medicament in the medicament container 1 can be calculated for a given geometry of the medicament container 1 and a given longitudinal position of the visual marker 6.1.

The marker 6.1 may be distinguishable from the stopper 4 material by its colour, e.g. by means of an optical sensor (not shown) arranged outside the medicament container 1.

The visual marker 6.1 may have the shape of a line or stripe as shown in FIG. 1 or the shape of another pattern. There may be only one or any other number of visual markers 6.1. The lines or stripes are preferably arranged in a circumferential direction of the stopper's lateral area.

The visual marker 6.1 may be applied, e.g. printed onto or embedded into the lateral area of the stopper 4.

Figure 3:
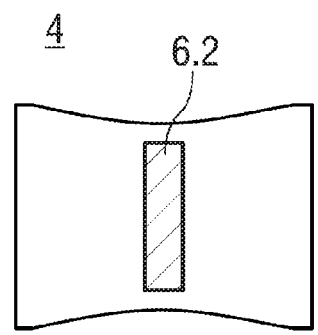
FIG. 3 is a stopper with an embedded magnetic marker.

FIG. 3 shows another embodiment of a stopper 4 with an embedded magnetic marker 6.2, e.g. a permanent magnet. The magnetic marker 6.2 may be detected by a magnetic sensor (not shown), such as a Hall sensor. By detecting a longitudinal position of the magnetic marker 6.2 a longitudinal position of the stopper 4 can be determined with high accuracy provided the location of the magnetic marker 6.2 with respect to the stopper 4 dimensions is defined. Hence a remaining quantity of the medicament in the medicament container 1 can be calculated for a given geometry of the medicament container 1 and a given longitudinal position of the magnetic marker 6.2.

There may be only one or any other number of magnetic markers 6.2.

Figure 4:
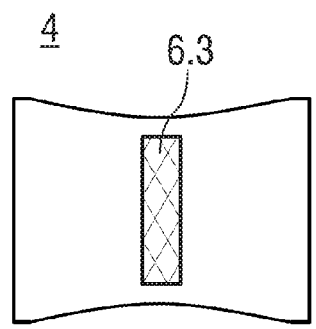
FIG. 4 is a stopper with an embedded electrically conductible marker.

FIG. 4 shows yet another embodiment of a stopper with an embedded electrically conductible marker 6.3, e.g. an iron core serving as a marker. Such a marker 6.3 may be detected by inducing an electrical current and measuring the consequently altered magnetic field. By detecting a longitudinal position of the marker 6.3 a longitudinal position of the stopper 4 can be determined with high accuracy provided the location of the marker 6.3 with respect to the stopper 4 dimensions is defined. Hence a remaining quantity of the medicament in the medicament container 1 can be calculated for a given geometry of the medicament container 1 and a given longitudinal position of the marker 6.3.

There may be only one or any other number of electrically conductible elements 6.3.

The stopper 4 may be applied in an insulin pen injector. The stopper may as well be applied in other injection devices and for different medicaments, e.g. one of an analgetic, an anticoagulant, an insulin derivate, heparin, Lovenox, a vaccine, a growth hormone, a peptide hormone, a proteine and complex carbohydrates.

There may be more than one compartment 5 and more than one stopper 4 in a medicament container 1, e.g. in an injector where two or more substances have to be stored separately but mixed prior to use.

The features of the embodiments of FIGS. 2 and 3 may be combined with each other, i.e. the stopper 4 may comprise both the microchip 6 and the sensitive coating.

Figure 5:
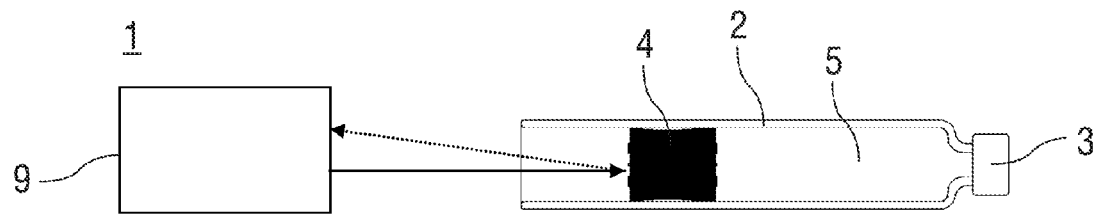
FIG. 5 is a medicament container with a laser triangulation sensor arranged behind the stopper.

FIG. 5 shows a medicament container 1 with a laser triangulation sensor 9 arranged distally from the stopper 4. The laser triangulation sensor 9 illuminates the distal or back side of the stopper 4 with a laser beam thereby creating a light spot. This light spot is detected by the laser triangulation sensor 9 and the distance between the laser triangulation sensor 9 and the stopper 4 is calculated by triangulation. The laser triangulation sensor 9 is linearly arranged behind the stopper 4.

Figure 6:
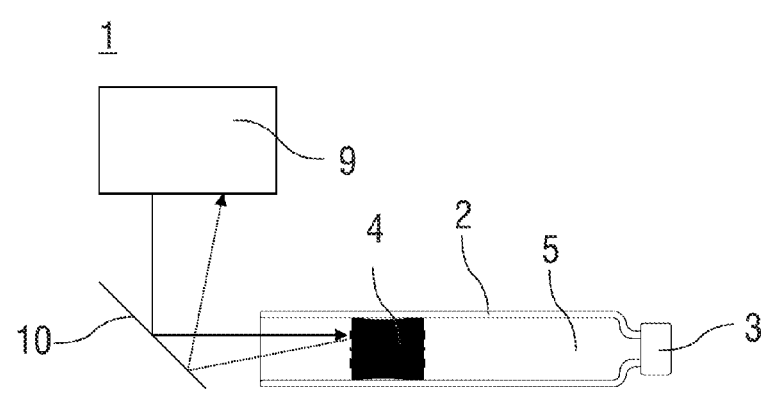
FIG. 6 is a medicament container with a mirror arranged behind the stopper for deflecting the optical path of the laser triangulation sensor.

FIG. 6 is a variant of the embodiment of FIG. 5. The laser beam from the laser triangulation sensor 9 to the stopper 4 and back is deflected by a mirror 10 arranged distally from the cylinder 2. The laser triangulation sensor 9 is arranged laterally. This embodiment allows for reducing the overall length of the arrangement.

Figure 7:
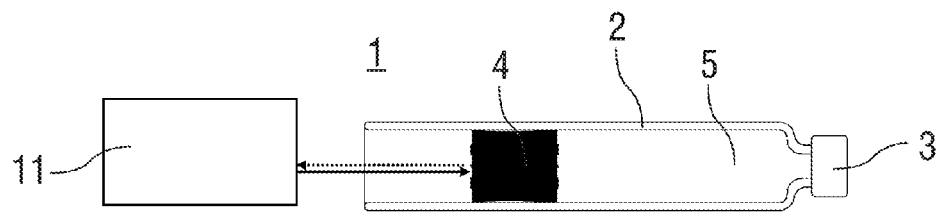
FIG. 7 is a medicament container with a chromatic confocal gauge.

FIG. 7 is a medicament container 1 with a chromatic confocal gauge 11 arranged distally from the stopper 4 for determining the distance between the chromatic confocal gauge 11 and the stopper 4. The distance is determined by emission of white light and measuring the dispersion of the light reflected by the stopper 4.

FIG. 8*a* is a lateral view of another embodiment of a medicament container 1. FIG. 8*b* is the related cross section through the stopper 4. A light sensitive sensor array 7 is arranged laterally from the cylinder 2 and parallely aligned. The sensor array 7 extends over almost the entire length of the cylinder 2. A light source 8 is arranged laterally from the cylinder 2 but angularly offset from the sensor array 7 in a manner to illuminate the cylinder 2. Two reflective visual markers 6.1 are circumferentially arranged on the stopper 4 for reflecting the light from the light source 8 to the sensor array 7. The intensity distribution of the light detected on the sensor array 7 indicates the stopper position. The number of visual markers 6.1 can be different from two. The light source 8 is preferably a surface emitting light source 8 extending over at least part of the length of the cylinder 2.

FIG. 9*a* is a lateral view of another embodiment of a medicament container 1. FIG. 9*b* is the related cross section through the stopper 4. A light sensitive sensor array 7 is arranged laterally from the cylinder 2 and parallely aligned. The sensor array 7 extends over almost the entire length of the cylinder 2. Two light sources 8 are arranged in the stopper 4 in a manner to illuminate the sensor array 7. The intensity distribution of the light detected on the sensor array 7 indicates the stopper position. The number of light sources 8 in the stopper 4 can be different from two.

Figure 10A:
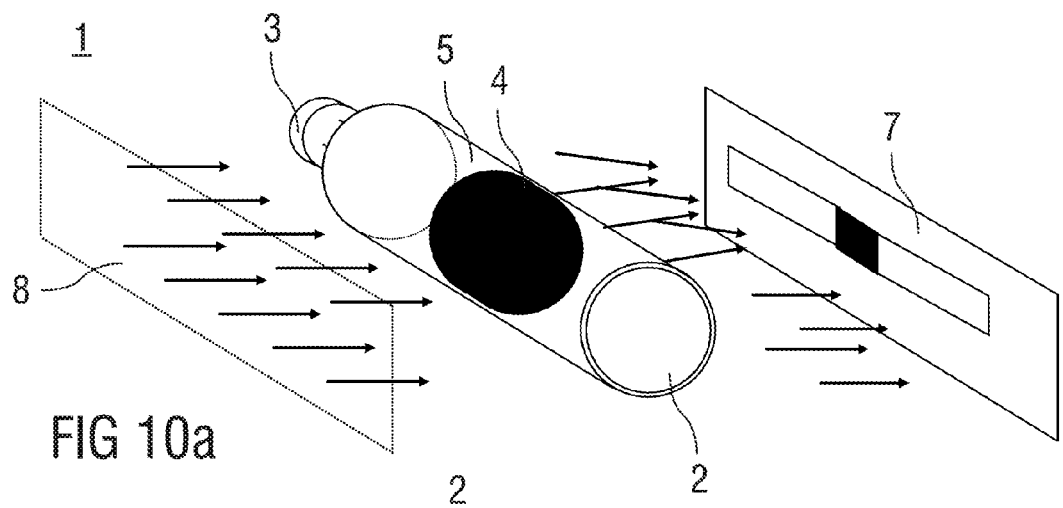
FIG. 10 is a medicament container with a laterally arranged light source and a sensor laterally arranged opposite the light source.
Figure 10B:
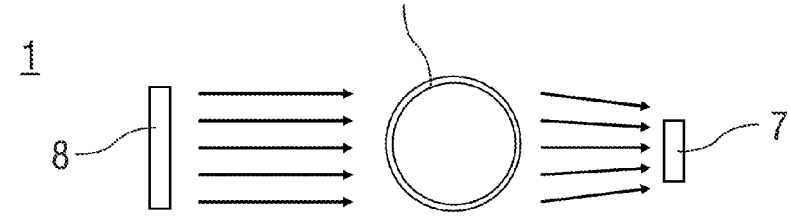
Figure 10C:
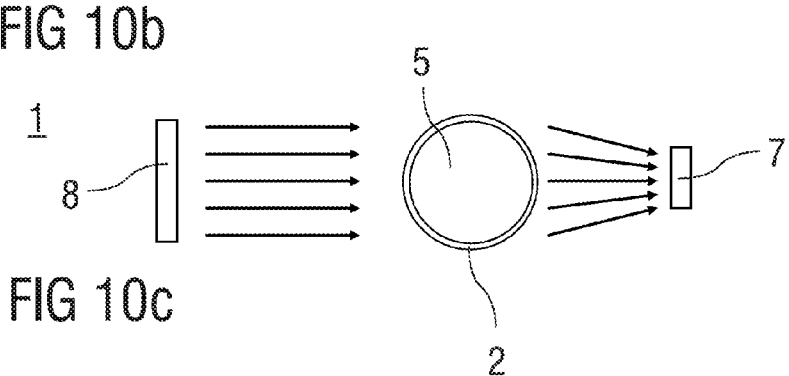
Figure 11:
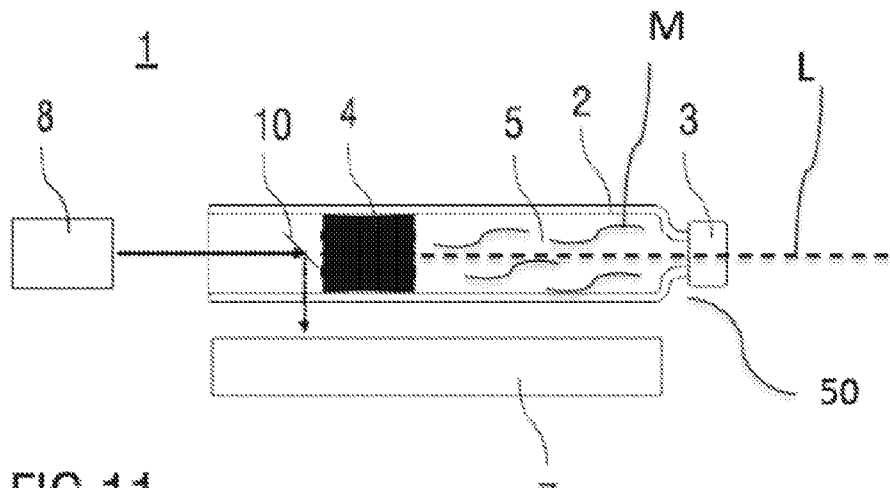
FIG. 11 is a medicament container with a mirror arranged behind the stopper for deflecting the light of a light source from behind the stopper to a laterally arranged sensor.

FIG. 10*a* is an isometric view of another embodiment of a medicament container 1. FIG. 10*b* is a related cross section through the cylinder 2 distally from the stopper 4. FIG. 10*c* is a related cross section through the cylinder 2 proximally from the stopper 4. A surface emitting light source 8 is arranged laterally from the cylinder 2 extending almost over the entire length of the cylinder 2 in a manner to shine into and through the cylinder 2. Opposite the light source 8 a light sensitive sensor array 7 is arranged for detecting the light from the light source 8 transmitted through the cylinder 2. The light is refracted in the cylinder 2, wherein the refraction index in the compartment 5 filled with the liquid medicament proximally from the stopper 4 is higher than the refractive index of the air filled part of the cylinder 2 distally from the stopper 4. Hence, the intensity of light detected by the sensor array 7 proximally from the stopper 4 is higher than distally from the stopper 4 thus allowing determining the longitudinal stopper position.

FIG. 11 is yet another embodiment of a medicament container 1 with a mirror 10 attached distally on the stopper 4 for deflecting the light of a light source 8 arranged distally to a laterally arranged sensor array 7. The resulting light spot on the sensor array 7 indicates the longitudinal position of the stopper 4.

Figure 12:
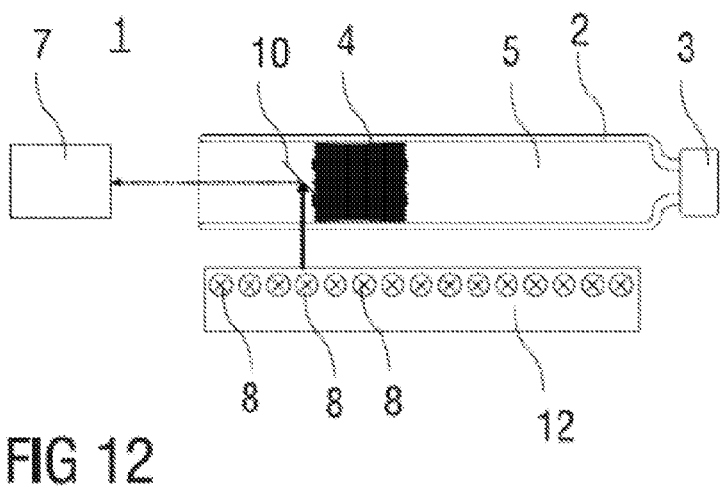
FIG. 12 is a medicament container with a mirror arranged behind the stopper for deflecting the light of a laterally arranged light source to a sensor arranged behind the stopper.

FIG. 12 is a medicament container 1 with a mirror 10 attached distally on the stopper 4 for deflecting the light of a laterally arranged array 12 of light sources 8 to a light sensitive sensor 7 arranged distally. The array 12 of light sources 8 extends over almost the entire length of the cylinder 2 and comprises a number of independent light sources 8, each of them arranged to be controlled independently and having a characteristic distinct from any other light source 8 in the array 12. The characteristic may be at least one wavelength of the light or a range of wavelengths. It may likewise be a modulation of the light such as a pulse frequency. Depending on the longitudinal stopper position the sensor 7 receives the light of one light source 8 or a small number of individual light sources 8. Due to the individual characteristic of the light of each light source 8 the longitudinal position of the stopper 4 can be determined.

Figure 13:
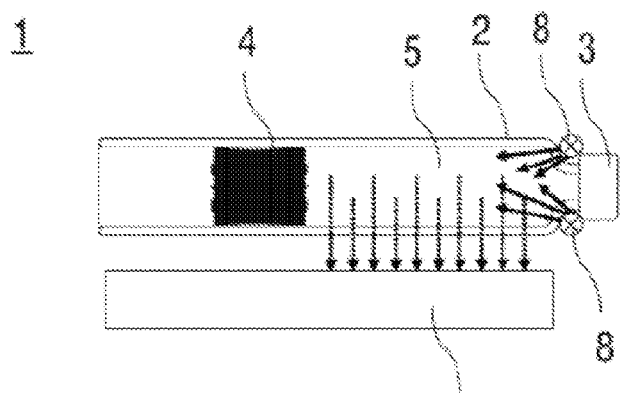
FIG. 13 is a medicament container with a circular light source arranged around a head of the medicament container and a laterally arranged sensor.

FIG. 13 is another embodiment of a medicament container 1 with a circular light source 8 arranged around a head of the medicament container 1 near the proximal end. The light source 8 emits light into the cylinder 2 and illuminates the medicament in the compartment 5 from the proximal end. A light sensitive sensor array 7 is arranged laterally from the cylinder 2 and parallely aligned. The sensor array 7 extends over almost the entire length of the cylinder 2. The cylinder 2 and/or the medicament is arranged to scatter the light so as to create a light/dark boundary on the sensor array 7 caused by the laterally scattered light and the opaque stopper 4. The light may be scattered by the medicament being a cloudy liquid such as cloudy insulin. The light may also be scattered by a non-transparent cylinder 2, i.e. a cylinder 2 which is translucent but not transparent.

The position of the light/dark boundary on the sensor array 7 represents the stopper position. The circular light source 8 may be an array 12 of light sources 8.

Figure 14:
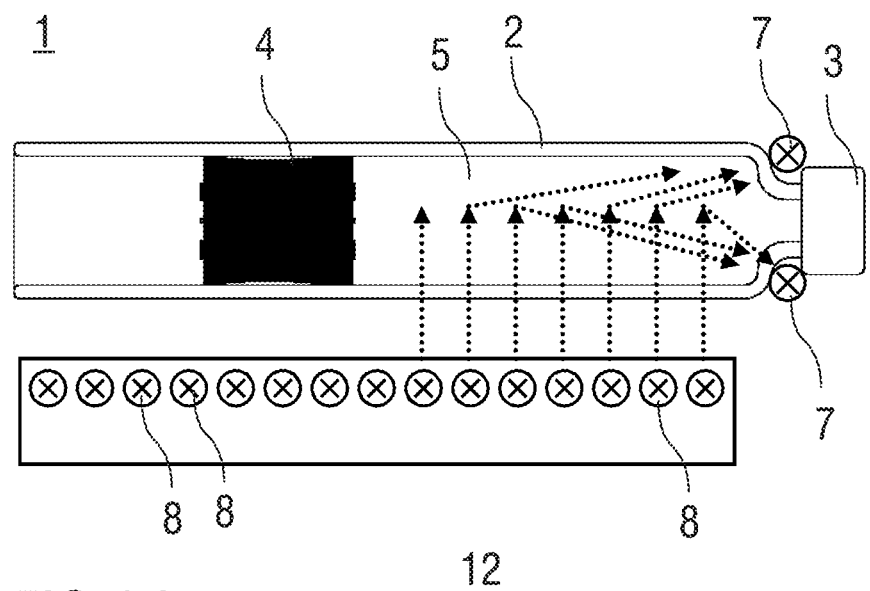
FIG. 14 is a medicament container with a laterally arranged light source and a circular sensor arranged around a head of the medicament container.

FIG. 14 is yet another embodiment of a medicament container 1 with a laterally arranged array 12 of light sources 8. The array 12 of light sources 8 extends over almost the entire length of the cylinder 2 and comprises a number of independent light sources 8, each of them arranged to be controlled independently and having a characteristic distinct from any other light source 8 in the array 12. The characteristic may be at least one wavelength of the light or a range of wavelengths. It may likewise be a modulation of the light such as a pulse frequency. A circular sensor 7 or array of sensors 7 is arranged around the head of the cylinder 2.

Depending on the longitudinal stopper position the compartment 5 and the medicament in the compartment 5 is illuminated by all or a fraction of the light sources 8. The cylinder 2 and/or the medicament is arranged to scatter the light so as to allow the sensor 7 or sensor array 7 to detect it. The light may be scattered by the medicament being a cloudy liquid such as cloudy insulin. The light may also be scattered by a non-transparent cylinder 2, i.e. a cylinder 2 which is translucent but not transparent.

The sensor 7 or array of sensors 7 receives the light of at least one light source 8 or fraction of individual light sources 8. A processor unit (not illustrated) connected to the sensor 7 or sensor array 7 has information on the allocation of each light source 8 and its characteristic and its position in the array 12. The processor unit is arranged to detect the characteristics of the light sources 8, determine which light source 8 is currently emitting light into the medicament container 1, conclude, that the light sources 8 whose characteristics are absent in the sensor data are currently obscured by the stopper 4, and determine the stopper position by comparing these conclusions to the information.

The longitudinal position of the stopper 4 in the medicament container 1 can be calculated from the determined distance between the stopper 4 and the respective sensor or gauge and a known relative position of the sensor/gauge and the medicament container 1.

The invention claimed is:

1. A system for use in determining a longitudinal position of a stopper within a medicament container comprising,
  a) a translucent medicament container containing a stopper and a liquid medicament, where the container has a length terminating at a head;
  b) a photo sensitive sensor that is laterally positioned next to the medicament container such that it extends over at least part of the length of the medicament container;
  c) a light source positioned in a circular manner around the head of the medicament container, where the light source is configured to emit light into the medicament container,
  wherein the medicament container is positioned relative to the photo sensitive sensor and light source such that light from the light source is scattered to allow the photo sensitive sensor to detect the scattered light, and
  wherein the photo sensitive sensor is electrically connected to a processor unit.

2. The system according to claim 1, characterized in that the processor unit is configured to determine the stopper position by detecting a light/dark boundary on the array of sensors caused by the scattered light and the stopper.

3. The system according to claim 1, characterized in that an array of light sources emits light with a characteristic distinct from the characteristics of the other light sources and where photo sensitive sensor is configured to detect the light of each light source, wherein the processor unit has information on the allocation of each light source and its characteristic and its position in the array, wherein the processor unit is arranged to:
  detect the characteristics of the light source,
  determine which light source is currently emitting light into the medicament container,
  conclude that the light sources whose characteristics are absent in the sensor data are currently obscured by the stopper, and
  determine the stopper position by comparing these conclusions to the information.

4. The system according to claim 1, characterized in that the characteristic of each light source is at least one wavelength of the light.

5. The system according to claim 1, characterized in that the characteristic of each light source is a modulation of the light.

6. The system according to claim 5, characterized in that the characteristic is a frequency or pattern of pulsed light.

7. The system according to claim 1, characterized in that the medicament is a cloudy liquid.

8. The system according to claim 1, characterized in that the medicament container is non-transparent.

9. The system according to claim 1, characterized in that the processor unit is arranged to determine a remaining quantity of the medicament in the medicament container from the longitudinal position of the stopper.

10. A system for use in determining a longitudinal position of a stopper within a medicament container comprising,
  a) a translucent medicament container containing a stopper and a liquid medicament, where the container has a length terminating at a head;
  b) a light source that is laterally positioned next to the medicament container such that it extends over at least part of the length of the medicament container, where the light source is configured to emit light into the medicament container;
  c) a photo sensitive sensor positioned in a circular manner around the head of the medicament container,
  wherein the medicament container is positioned relative to the photo sensitive sensor and light source such that light from the light source is scattered to allow the photo sensitive sensor to detect the scattered light, and
  wherein the photo sensitive sensor is electrically connected to a processor unit.

11. The system according to claim 10, characterized in that a ring of photo sensitive sensors is arranged around the head of the medicament container.

12. The system according to claim 10, characterized in that the processor unit is configured to determine the stopper position by detecting a light/dark boundary on the array of sensors caused by the scattered light and the stopper.

13. The system according to claim 10, characterized in that an array of light sources emits light with a characteristic distinct from the characteristics of the other light sources and where the photo sensitive sensor is configured to detect the light of each light source, wherein the processor unit has information on the allocation of each light source and its characteristic and its position in the array, wherein the processor unit is arranged to:
  detect the characteristics of the light sources,
  determine which light source is currently emitting light into the medicament container,
  conclude that the light sources whose characteristics are absent in the sensor data are currently obscured by the stopper, and determine the stopper position by comparing these conclusions to the information.

14. The system according to claim 10, characterized in that the characteristic of each light source is at least one wavelength of the light.

15. The system according to claim 10, characterized in that the characteristic of each light source is a modulation of the light.

16. The system according to claim 15, characterized in that the characteristic is a frequency or pattern of pulsed light.

17. The system according to claim 10, characterized in that the medicament is a cloudy liquid.

18. The system according to claim 10 characterized in that the medicament container is non-transparent.

19. The system according to claim 10, characterized in that the processor unit is arranged to determine a remaining quantity of the medicament in the medicament container from the longitudinal position of the stopper.

\* \* \* \* \*